United States Patent [19]

Grau

[11] Patent Number: 5,628,723
[45] Date of Patent: May 13, 1997

[54] EMERGENCY BANDAGE

[76] Inventor: Bernard Grau, 3/45 Kibbutz Galuyot Street, Jerusalem, Israel

[21] Appl. No.: 601,224

[22] Filed: Feb. 14, 1996

Related U.S. Application Data

[63] Continuation-in-part of Ser. No. 336,011, Nov. 8, 1994, abandoned, which is a continuation of Ser. No. 974,377, Nov. 10, 1992, abandoned, which is a continuation of Ser. No. 753,120, Aug. 30, 1991, abandoned.

[51] Int. Cl.[6] .............................. A61F 13/00; A61B 17/00
[52] U.S. Cl. ................................................ 602/53; 606/203
[58] Field of Search .................................. 602/41, 53, 75; 606/201, 203

[56] References Cited

U.S. PATENT DOCUMENTS

| | | |
|---|---|---|
| 34,112 | 1/1862 | Lambert . |
| 721,162 | 2/1903 | Derain . |
| 1,870,052 | 8/1932 | Jones ........................ 606/203 |
| 1,877,885 | 9/1932 | Kerngood . |
| 2,113,534 | 4/1938 | Brown . |
| 2,480,430 | 8/1949 | Walters . |
| 2,646,034 | 7/1953 | Chapudos . |
| 2,815,752 | 12/1957 | Forman . |
| 3,005,454 | 10/1961 | Bird . |
| 3,050,064 | 8/1962 | Moore et al. . |
| 3,327,361 | 6/1967 | Mathison . |
| 3,536,068 | 10/1970 | Stubbs . |
| 4,048,991 | 9/1977 | Marx . |
| 4,149,540 | 4/1979 | Hasslinger . |
| 4,243,028 | 1/1981 | Payana . |
| 4,345,591 | 8/1982 | Hedgren . |
| 4,427,007 | 1/1984 | Rexroth . |
| 4,528,700 | 7/1985 | Johnson . |
| 4,802,667 | 2/1989 | Altner . |
| 4,843,689 | 7/1989 | Fildan . |
| 5,065,773 | 11/1991 | Jackson et al. . |
| 5,234,459 | 8/1993 | Lee . |
| 5,312,350 | 5/1994 | Jacobs ........................ 606/203 |

FOREIGN PATENT DOCUMENTS 3813415  8/1989  Germany .

*Primary Examiner*—Mary Beth Jones
*Attorney, Agent, or Firm*—Helfgott & Karas, P.C.

[57] ABSTRACT

For use in a bandage comprising a sterile dressing and a web portion attached to and extending from the sterile dressing, a pressure enhancement member comprising a base, and at least one wrapping element generally perpendicular to the base, the at least one wrapping element having a gap, wherein the pressure enhancement member is attached to a non-wound-side surface of the sterile dressing, and the at least one wrapping element is arranged for wrapping therearound by the web portion, wherein when the web portion is wrapped in a first direction around a limb having thereon a wound, and forced through the gap, and the web portion is then wrapped around the at least one wrapping element in a second direction, the pressure enhancement member applies a pressure on the dressing, thereby causing the dressing to apply a local pressure to the wound, and subsequent wrappings of the web portion on the pressure enhancement member, on previous wrappings of the web portion and on the limb, increase the local pressure on the wound.

20 Claims, 15 Drawing Sheets

EMERGENCY BANDAGE

FIELD OF THE INVENTION

The present invention relates to bandages and mechanical assemblies for use therewith.

BACKGROUND OF THE INVENTION

This application is a continuation-in-part of application Ser. No. 08/336,011 filed on Nov. 8, 1994, now abandoned, which is a continuation of application Ser. No. 974,377 filed on Nov. 10, 1992, now abandoned, which is a continuation of application Ser. No. 753,120, filed on Aug. 30, 1991, now abandoned.

The purpose of bandages is to protect exposed wounds and, in relation to certain types of wounds, to prevent loss of blood. Bandages are packaged to be carried and used by military personnel, police, ambulances, hikers and campers, for example, and may also be part of first-aid kits, for use in factories, offices and the home.

It is known to use bandages with attached dressing pads, which saves time otherwise expended in assembling a separate dressing pad and securing it under the bandage. U.S. Pat. Nos. 34,112, 721,162, 2,113,534, 2,480,430, 2,646,034, 3,005,454, 3,050,064, 3,536,068, 4,048,991, 4,149,540, 4,243,028, 4,345,591, 4,802,667 and 5,234,459 are believed to be representative of prior art bandages, fasteners, straps, belts or other apparatus which may be useful for applying a bandage by an individual.

SUMMARY OF THE INVENTION

The present invention seeks to provide improved bandages and pressure enhancement members therefor, and improved methods for dressing wounds.

There is thus provided in accordance with a preferred embodiment of the present invention, for use in a bandage including a sterile dressing and a web portion attached to and extending from the sterile dressing, a pressure enhancement member including a base, and at least one wrapping element generally perpendicular to the base, the at least one wrapping element having a gap, wherein the pressure enhancement member is attached to a non-wound-side surface of the sterile dressing, and the at least one wrapping element is arranged for wrapping therearound by the web portion, wherein when the web portion is wrapped in a first direction around a limb having thereon a wound, and forced through the gap, and the web portion is then wrapped around the at least one wrapping element in a second direction, the pressure enhancement member applies a pressure on the dressing, thereby causing the dressing to apply a local pressure on the wound, and subsequent wrappings of the web portion on the pressure enhancement member, on previous wrappings of the web portion and on the limb, increase the local pressure on the wound.

In accordance with a preferred embodiment of the present invention, at least one of the base and the at least one wrapping element has a notch formed thereon, wherein at least one of the subsequent wrappings of the web portion is wrapped against the notch.

Additionally in accordance with a preferred embodiment of the present invention, the pressure enhancement member includes two wings which are separated from each other by the gap.

Further in accordance with a preferred embodiment of the present invention, the wings are resilient in a direction which facilitates forcing the web portion through the gap, and wherein the wings are configured such that once the web portion is forced through the gap, the web portion is substantially prevented from escaping the gap inadvertently.

Additionally in accordance with a preferred embodiment of the present invention, the at least one wrapping element is roughened.

Alternatively in accordance with a preferred embodiment of the present invention, the pressure enhancement member includes a plurality of wrapping elements arranged in a pattern such that the web portion is wrappable around and between the wrapping elements.

There is also provided in accordance with a preferred embodiment of the present invention, a bandage including a sterile dressing, a web portion attached to and extending from the sterile dressing, and a pressure enhancement member attached to a non-wound-side surface of the sterile dressing, the pressure enhancement member including a base and at least one wrapping element generally perpendicular to the base, the at least one wrapping element having a gap, and the at least one wrapping element being arranged for wrapping therearound by the web portion, wherein when the web portion is wrapped in a first direction around a limb having thereon a wound, and forced through the gap, and the web portion is then wrapped around the at least one wrapping element in a second direction, the pressure enhancement member applies a pressure on the dressing, thereby causing the dressing to apply a local pressure on the wound, and subsequent wrappings of the web portion on the pressure enhancement member, on previous wrappings of the web portion and on the limb, increase the local pressure on the wound.

In accordance with a preferred embodiment of the present invention, the bandage further includes a hooking dowel attached to an end of the web portion, for securing the bandage after wrapping around the limb.

Preferably the hooking dowel includes at least one prong which engages a portion of the web portion.

The hooking dowel may be twisted together with a portion of the web portion, thereby applying a tourniquet to the wound.

There is also provided in accordance with a preferred embodiment of the present invention, a method for dressing a wound on a limb, the method including the steps of:

providing a bandage, the bandage including a sterile dressing, a web portion attached to and extending from the sterile dressing, and a pressure enhancement member attached to a non-wound-side surface of the sterile dressing, the pressure enhancement member including a base and at least one wrapping element generally perpendicular to the base, the at least one wrapping element having a gap, and the at least one wrapping element being arranged for wrapping therearound by the web portion;

wrapping the web portion in a first direction around the limb;

forcing the web portion through the gap;

wrapping the web portion around the at least one wrapping element in a second direction, thereby causing the pressure enhancement member to apply a pressure on the dressing, thereby causing the dressing to apply a local pressure on the wound; and wrapping the web portion around the limb and the pressure enhancement member, thereby causing subsequent wrappings of the web portion on the pressure enhancement member, on previous wrappings of the web portion and on the limb, to increase the local pressure on the wound.

The second direction may be generally opposite to the first direction. Alternatively, the second direction may be generally perpendicular to the first direction.

In accordance with a preferred embodiment of the present invention, the base is generally parallel to the wound when wrapping the web portion in the first direction, and wherein the base is brought generally perpendicular to the wound when wrapping the web portion in the second direction.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1A:
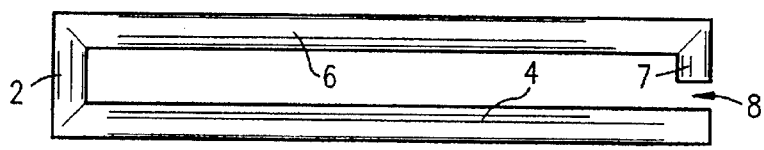
FIGS. 1A–1D are simplified illustrations of four embodiments of a frame member useful in the practice of the present invention.

Reference is now made to FIGS. 1A–1D which are simplified illustrations of four embodiments of a frame member useful in the practice of the present invention. The frame member illustrated in FIG. 1A includes at least one side section 2 integral with a base section 4, a top section 6, an integral partial section 7, and an open portion 8 at the side remote from the side section 2. The frame member illustrated in FIG. 1A may be regarded as having substantially the shape of an elongated rectangle with part of one short side absent.

Figure 1B:
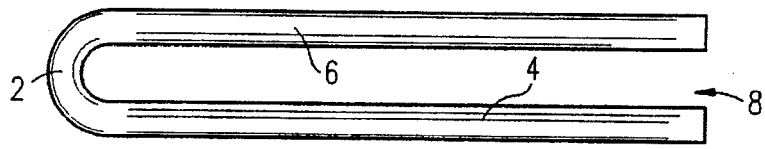

The frame member illustrated in FIG. 1B is substantially the same as the frame member of FIG. 1A, except that in the embodiment of FIG. 1B there is no partial section 7. The embodiment of FIG. 1B may be regarded as having substantially the shape of an elongated U. In the frame member of FIG. 1B, top section 6 may be terminated by a partial side section (whether straight or curved) analogous to that of FIG. 1A, if desired. The optional partial side sections of the frame member serve to enable improved retention of a web of a bandage (not shown).

Figure 1C:
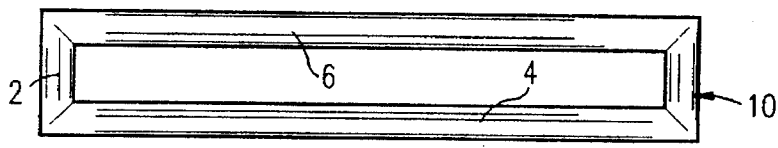
Figure 1D:
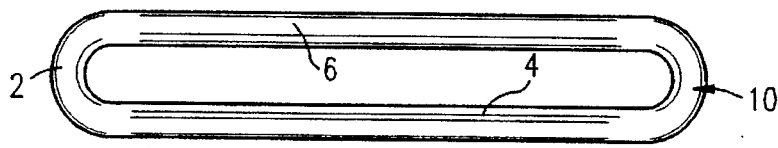

In a different embodiment of the frame member, the at least one side section comprises a first side section integral with the base section and the top section, and a second side section remote from the first side section. As illustrated in FIGS. 1C and 1D, the second side section 10 may be integral with the base and top sections (4 and 6, respectively). The frame member illustrated in FIG. 1C may be regarded as having substantially the shape of an elongated rectangle, whereas that illustrated in FIG. 1D may be regarded as being substantially elliptical in shape.

Figure 2A:
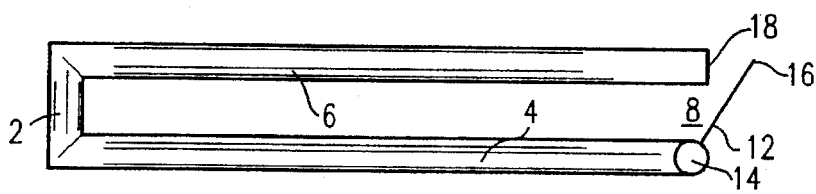
FIGS. 2A–2H are simplified illustrations of eight further embodiments of the frame member useful in the practice of the present invention.
Figure 2B:
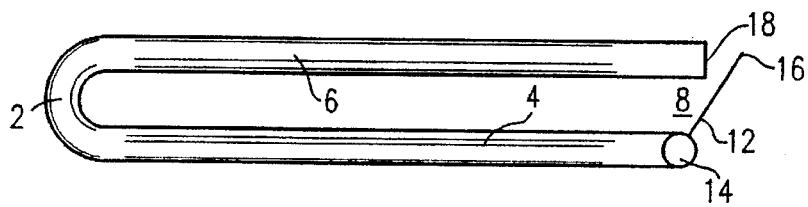

Referring now to FIGS. 2A and 2B, it is seen that alternatively, the second side section 12 may be discrete and includes means for fastening it to the base and top sections. Thus, by way of example, the discrete second side section may be hinged at 14, whereby the open portion 8 may be opened or closed, and the top end 16 may be fastened to the end 18 of top section 6 in any convenient manner (not shown) e.g. magnetically or by a hook and peg, and so forth. The frame member illustrated in FIG. 2A may be regarded as having substantially the shape of an elongated rectangle (when 12 is in the closed position and 16 is fastened at 18), whereas that illustrated in FIG. 2B may be regarded as having substantially the shape of an elongated U with the open end closable by straight element 12. In a variation of the frame member shown in FIG. 2B, element 12 may be curved, such that e.g. the frame member may be regarded as being substantially elliptical in shape.

Figure 2C:
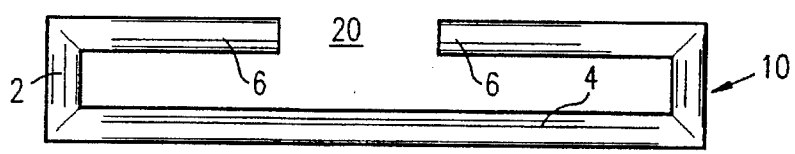
Figure 2D:
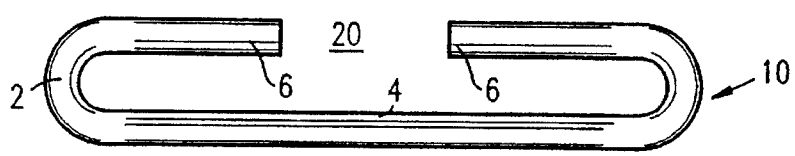

In yet a different embodiment of the frame member illustrated in FIGS. 2C and 2D, the at least one side section comprises a first side section 2 integral with the base and top sections, 4 and 6 respectively, and a second side section 10 remote from the first side section and integral with the base and top sections, the top section being characterized by having a gap 20 in the continuity thereof, thereby to enhance the ease with which the web is threaded through the internal space. The frame member illustrated in FIG. 2C may be regarded as having substantially the shape of an elongated rectangle with a gap in one of the elongated sides thereof, whereas that illustrated in FIG. 2D may be regarded as being substantially elliptical in shape with a gap in one of the elongated portions thereof. The gap 20 may be provided with closure means (not shown).

The frame member preferably performs a particular function in the bandage of the invention. In any of the embodiments illustrated in FIGS. 1A–1D and 2A–2D, for example, base section 4 is attached to, or adjacent to, the web (not shown) with its length across the width of the web, in any suitable manner, e.g. by use of stitching or adhesive, or by threading one layer of web through the internal space of the frame member and adhering or stitching an added piece of material on the outside of 4 so as to secure the latter between the web and the material. It will be appreciated that the condition referred to herein that the internal space must be such that the web may be threaded therethrough is to be understood as after attachment of 4 to the web, so that depending on the particular manner in which such attachment is effected, the internal space of the frame member may need to accommodate in absolute terms more than one thickness of the web.

Figure 2E:
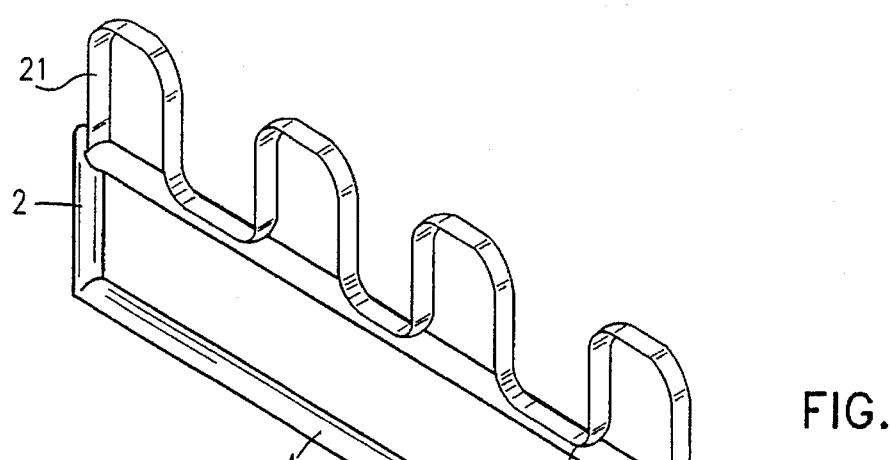
Figure 2F:
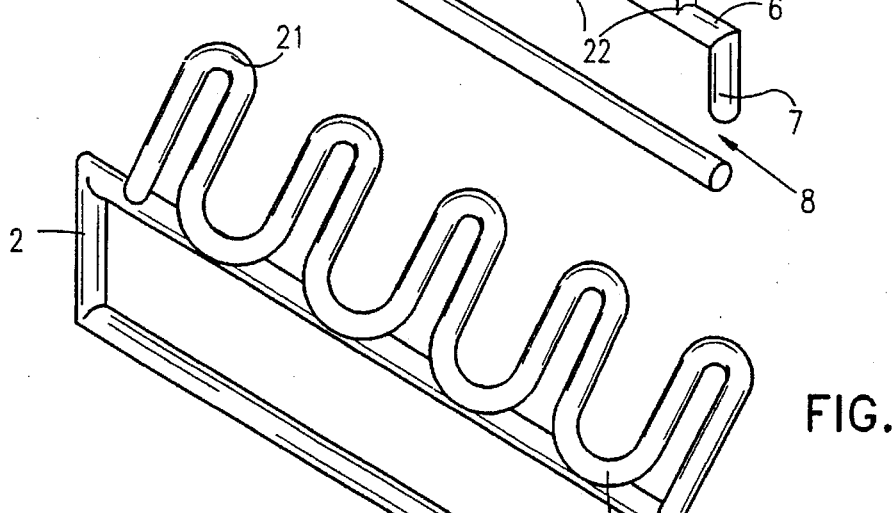
Figure 2G:
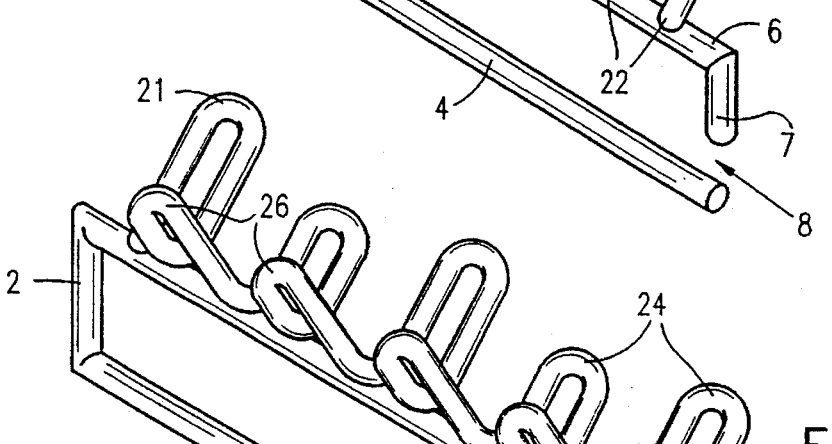

In the embodiments of the invention illustrated in FIGS. 2E, 2F and 2G (in which the same reference numerals as used previously have the same meaning as has been described hereinabove), an integral member indicated at 21 functions to exert pressure on the wound when the bandage is applied as described, and in any event makes unnecessary the use of the at least partially rotatable elongate member as described in respects of certain embodiments herein. While other configurations of member 21 will suggest themselves to skilled persons, in the illustrated embodiments of FIGS.

2E, 2F and 2G this member has a more or less wave-like form, which may be, e.g., welded at all points (e.g., at 22) touching top section 6, or alternatively it could be welded only at each end of 21 thus imparting a spring-like character thereto. Member 21 in FIG. 2E is made from an elongate metal strip, whereas in FIGS. 2F and 2G it is made from an elongate metal rod. In FIG. 2E, also, member 21 is generally coplanar with the plane of the frame member, whereas in FIG. 2F it is disposed at an angle thereto. In FIG. 2G, alternate loops of member 21 are in planes which are e.g. at 90 degrees to each other, i.e. for example loops 24 are in one plane whereas loops 26 are in a plane at right-angles thereto, the planes of both sets of loops being non-coplanar with the plane of the frame member. It will also be evident that this kind of feature of an integral member 21 could equally be utilized where the basic frame member has the configuration depicted in (e.g.) any of FIGS. 1A, 1B, 1C, 1D, 2A and 2B.

Figure 2H:
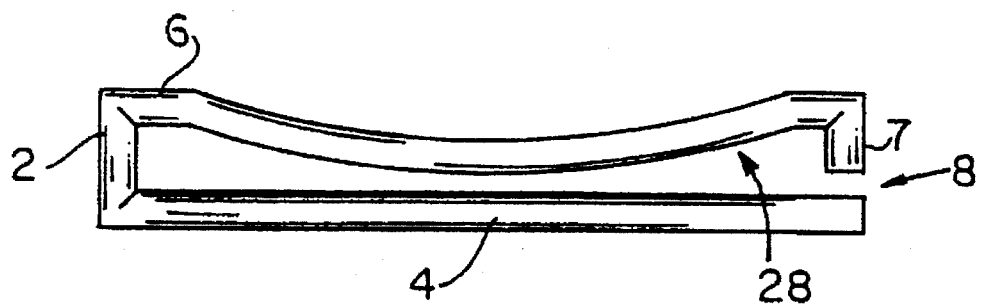

FIG. 2H illustrates an embodiment in which the generally central part (e.g. the central two-thirds of the length) of top section 6 of the frame member of FIG. 1A has been made inwardly curving as shown at 28. Such a configuration, which prevents bunching of the web and thus maintains its constant width, could equally be utilized where the basic frame member has the configuration depicted in (e.g.) any of FIGS. 1A, 1B, 1C, 1D, 2A and 2B.

In the embodiments of the frame member shown in FIGS. 2E, 2F, 2G and 2H, there is a gap 8 in its continuity, enabling ready threading of the frame member by the web member. It will however be apparent that these embodiments can be adapted, e.g., by replacing gap 8 by a gap in the top section of the frame member, such as has been shown in FIGS. 2C and 2D.

The frame member may be fabricated from any suitable material having the necessary mechanical strength to resist substantial distortion of its shape when the web is pulled against the top side 6. Persons skilled in the art will appreciate that, e.g., stainless steel and other metals and alloys, as well as tough generally inflexible plastics, may be suitable for this purpose.

Figure 3:
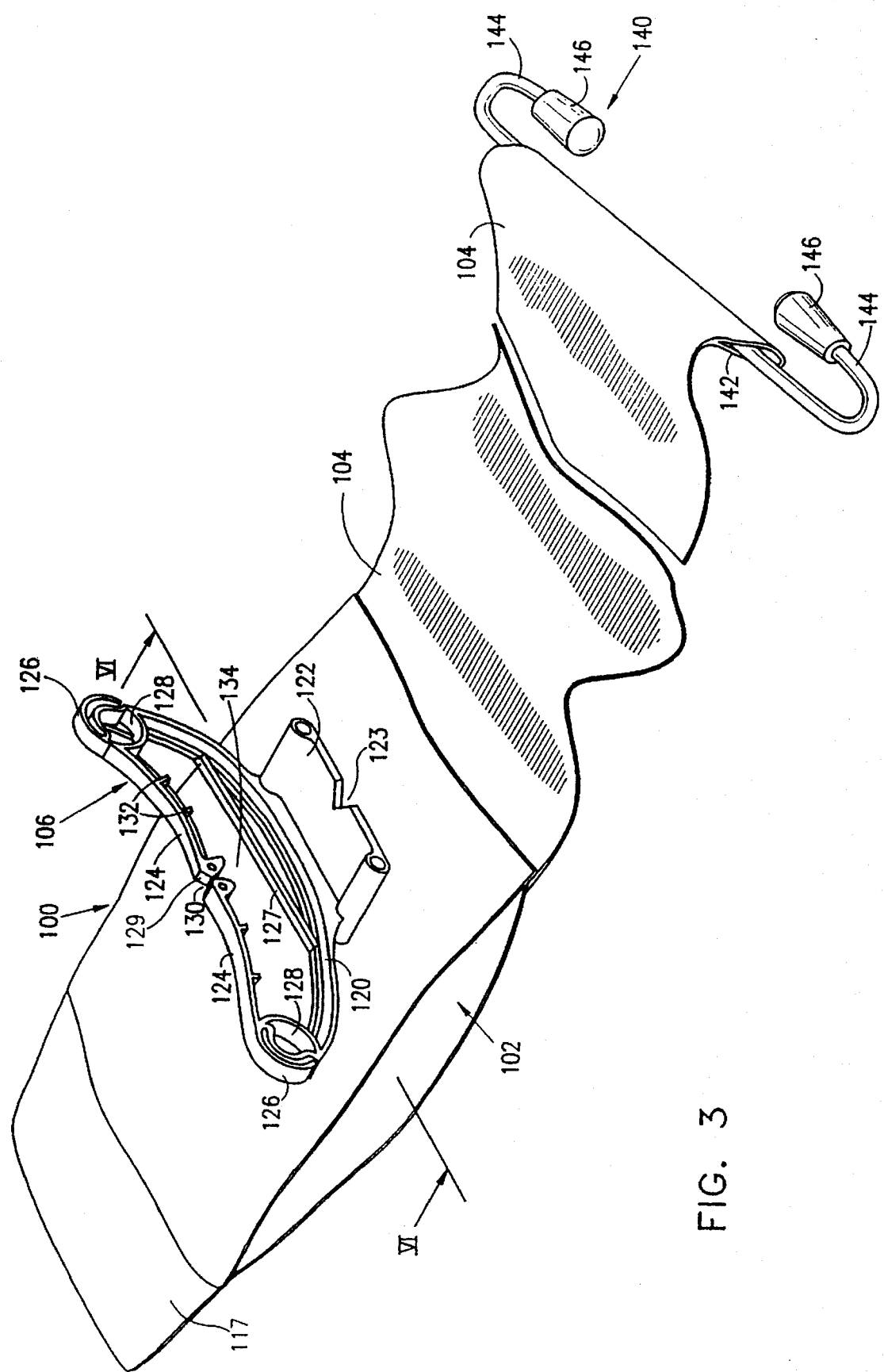
FIG. 3 is a partial simplified pictorial illustration of a bandage, constructed and operative in accordance with another preferred embodiment of the present invention.
Figure 6:
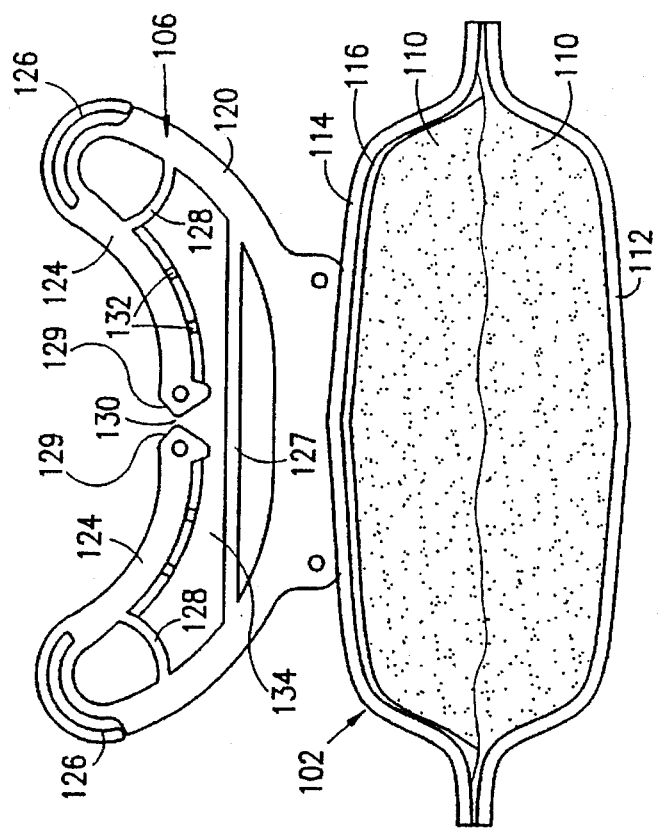
FIG. 6 is a simplified sectional illustration of the bandage of FIG. 3, taken along lines VI—VI in FIG. 3.

Reference is now made to FIGS. 3 and 6 which illustrate a bandage 100, constructed and operative in accordance with another preferred embodiment of the present invention. Bandage 100 includes a sterile dressing 102, a web portion 104 and a pressure enhancement member 106.

As seen in FIG. 6, dressing 102 preferably includes one or more soft, absorbent portions 110, typically made of cotton, sandwiched between a sterile non-adherent pad 112 and a structural layer 114. Pad 112 is adapted to be placed on an open wound. Structural layer 114 is typically made of polyamide and is adapted for mounting thereon pressure enhancement member 106. Web portion 104 is an extension of structural layer 114. A blood dispersing barrier 116, preferably made of plastic, may be placed between structural layer 114 and absorbent portion 110, as seen in FIG. 6.

As seen in FIG. 3, an additional web portion 117 may be attached to dressing 102 on a side opposite to web portion 104. Web portion 117, which typically extends about 2 cm from dressing 102, may be grasped when applying bandage 100 on a wound.

Pressure enhancement member 106 may employ any of the frame members illustrated in FIGS. 1A–2H. However, a preferred embodiment will now be described.

Pressure enhancement member 106 is preferably made of a flexible, resilient material, such as a structural plastic, and includes a bow-shaped portion 120 fixedly attached to a base 122 and generally perpendicular thereto. Base 122 may have a notch 123 formed thereon. Two arcuate upper wings 124 are joined to bow-shaped portion 120 at rounded junctions 126, as shown in FIGS. 3 and 6. Bow-shaped portion 120 and upper wings 124 form a wrapping element. Pressure enhancement member 106 is mounted on dressing 102 such that upper wings 124 and bow-shaped portion 120 curve away from dressing 102.

Near each rounded junction 126 is preferably an arcuate stiffening rib 128, as seen in FIGS. 3 and 6. The purpose of stiffening ribs 128 will be described hereinbelow with reference to FIG. 10A.

Bow-shaped portion 120 may be provided with an additional stiffening rib 127, located intermediate the bottom of bow-shaped portion 120 and upper wings 124.

Upper wings 124 are preferably chamfered at tips 129 which are separated from each other by a gap 130. Roughening ribs 132 may be provided along upper wings 124. The purpose of chamfered tips 129 and roughening ribs 132 will be described hereinbelow with reference to FIGS. 9 and 10A, respectively. Upper wings 124 and bow-shaped portion 120 define therebetween a space 134.

As seen in FIG. 3, a hooking dowel 140 is preferably attached to an end 142 of web portion 104. Hooking dowel 140 preferably comprises a pair of opposing hooks 144. An end 146 of each hook 144 may be covered with a material such as plastic or rubber, if desired.

Figure 4:
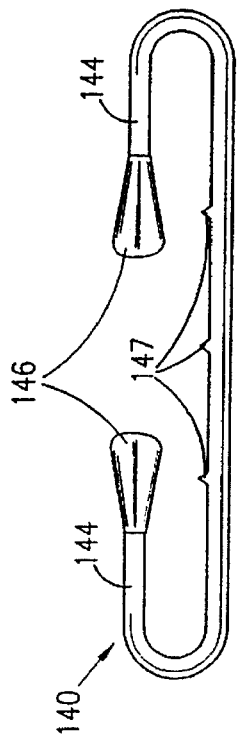
FIG. 4 is a simplified illustration of a hooking dowel useful in the bandage of FIG. 3.

Reference is now made to FIG. 4 which illustrates hooking dowel 140 removed from web portion 104. It is seen that hooking dowel 140 preferably includes one or more prongs 147. Prongs 147 engage web portion 104, thereby helping to prevent bunching and sliding of web portion 104.

Figure 5A:
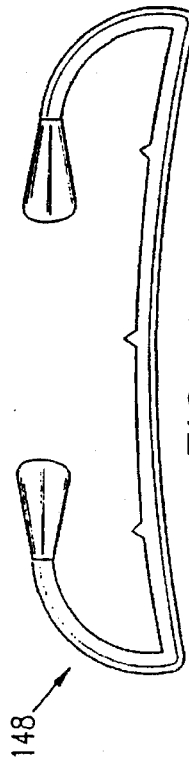
FIGS. 5A and 5B are simplified illustrations of two other hooking dowels useful in the bandage of FIG. 3.
Figure 5B:
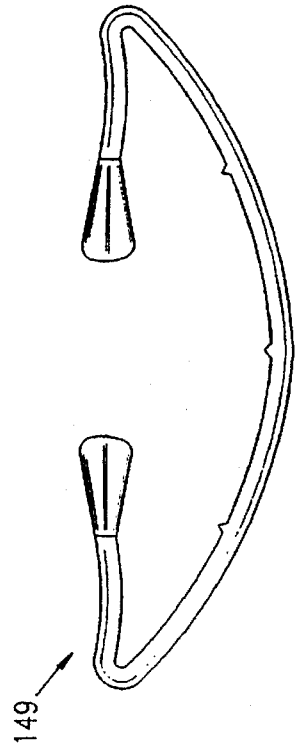

It is appreciated that various configurations of hooking dowels are possible. FIGS. 5A and 5B illustrate two other hooking dowels 148 and 149, respectively, useful in the bandage of FIG. 3.

Reference is now made to FIGS. 7–12 which are simplified pictorial illustrations of bandaging a wound with bandage 100.

Figure 7:
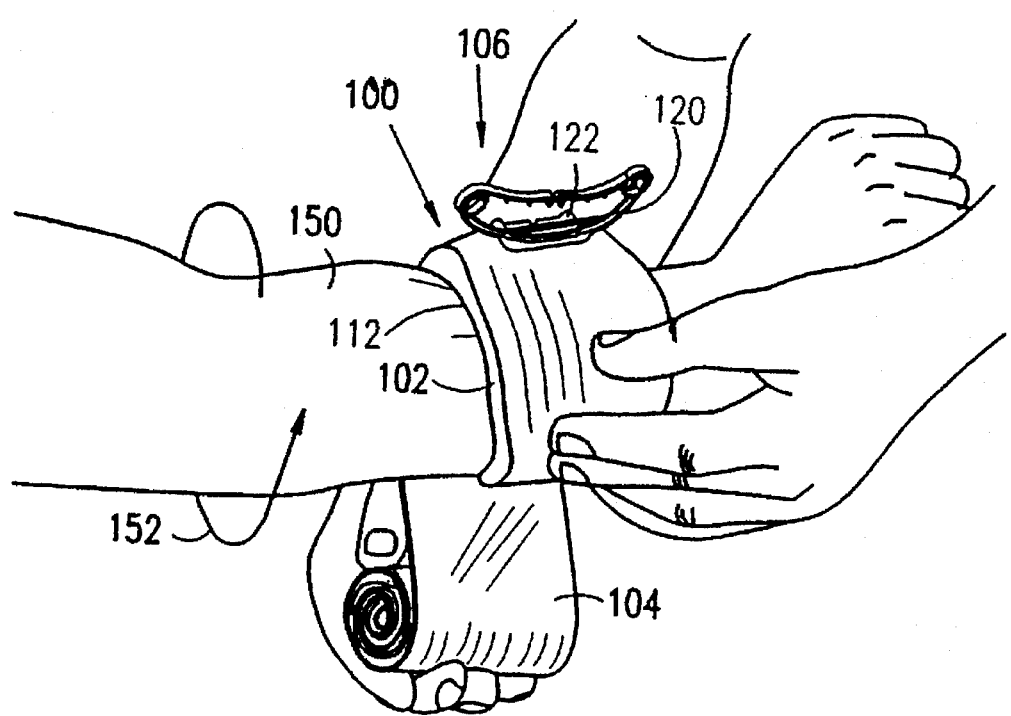
FIGS. 7–12 are simplified pictorial illustrations of bandaging a wound using the bandage of FIG. 3.

As seen in FIG. 7, pad 112 of dressing 102 of bandage 100 is placed on a wounded limb 150 with bow-shaped portion 120 of pressure enhancement member 106 extending generally perpendicularly away from the wound area and base 122 lying generally flat on dressing 102. Pressure enhancement member 106 is thus located over the wound site. In FIG. 7, a user is shown starting to wrap web portion 104 around wounded limb 150 in the direction of an arrow 152.

Figure 8:
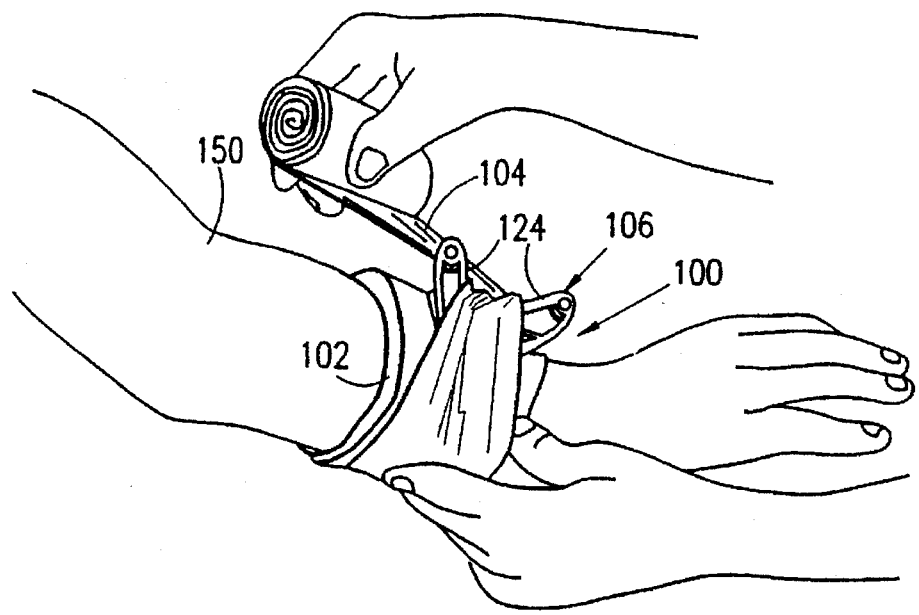

In FIG. 8, web portion 104 has been wrapped once around wounded limb 150 and is brought tightly against upper wings 124 of pressure enhancement member 106.

Figure 9:
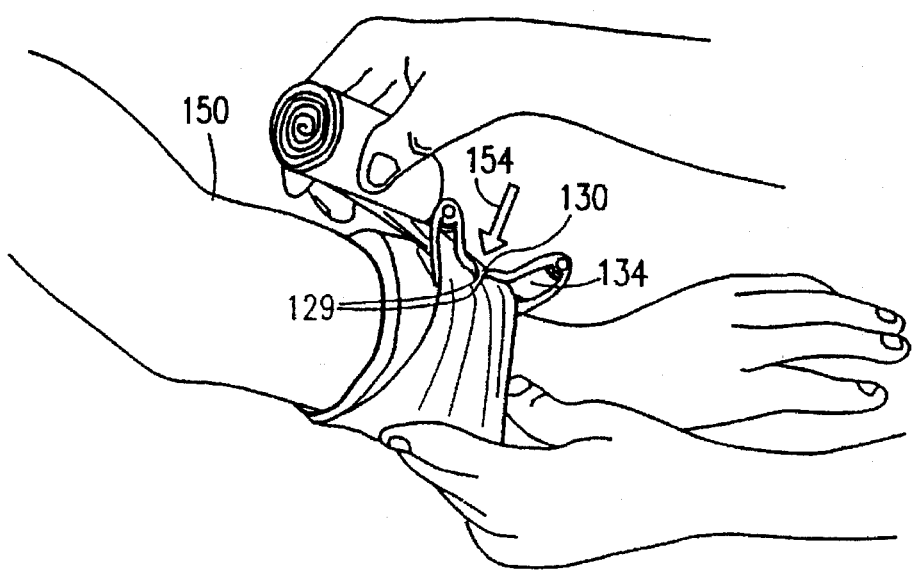

In FIG. 9, web portion 104 is pressed in the direction of an arrow 154 against upper wings 124 such that web portion 104 is pushed through gap 130 into space 134. It is a particular feature of the present invention that the resiliency of upper wings 124 facilitates pushing web portion 104 through gap 130. Chamfered tips 129 also facilitate pushing web portion 104 through gap 130. Web portion 104 is preferably made of a material which allows web portion 104 to stretch back to nearly full width after being forced through gap 130.

Figure 10A:
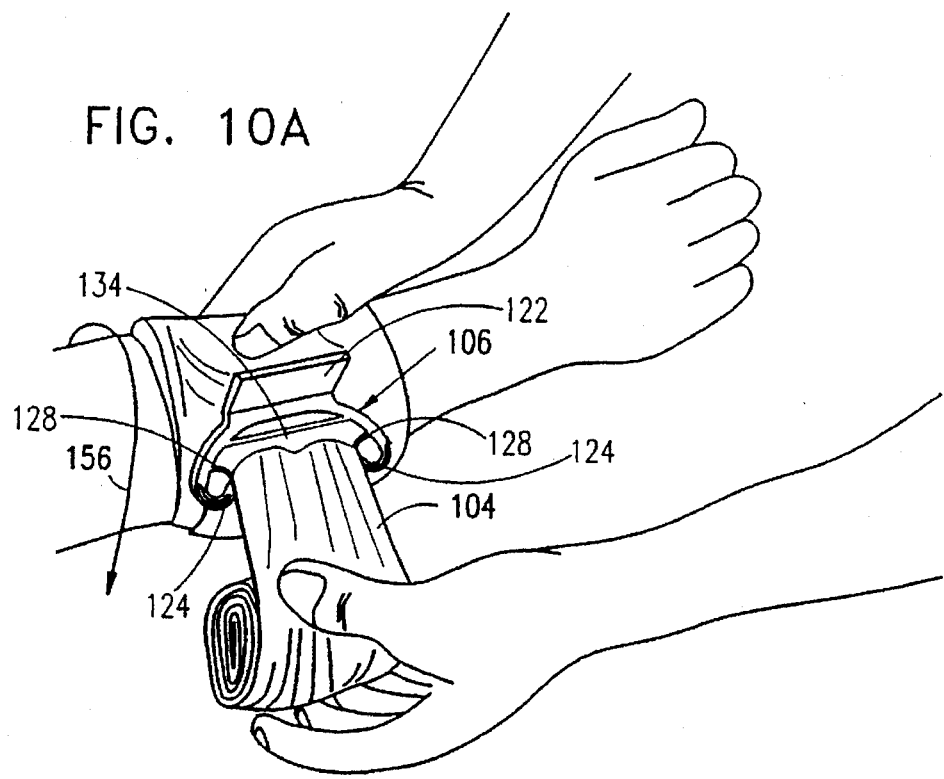

In FIG. 10A, web portion 104 is tightly pulled back against pressure enhancement member 106 in the direction of an arrow 156, opposite to the direction of arrow 152 (FIG. 7), thereby forcing pressure enhancement member 106 down against dressing 102 and applying pressure to the wounded area. It is noted that base 122 now extends generally perpendicularly away from the wound area and bow-shaped portion 120 now lies generally flat on dressing 102. Thus, the orientation of pressure enhancement member 106 with respect to the wounded area changes when web portion 104 is pulled in the direction of arrow 156. The elasticity of structural layer 114 facilitates this change in orientation.

Figure 10B:
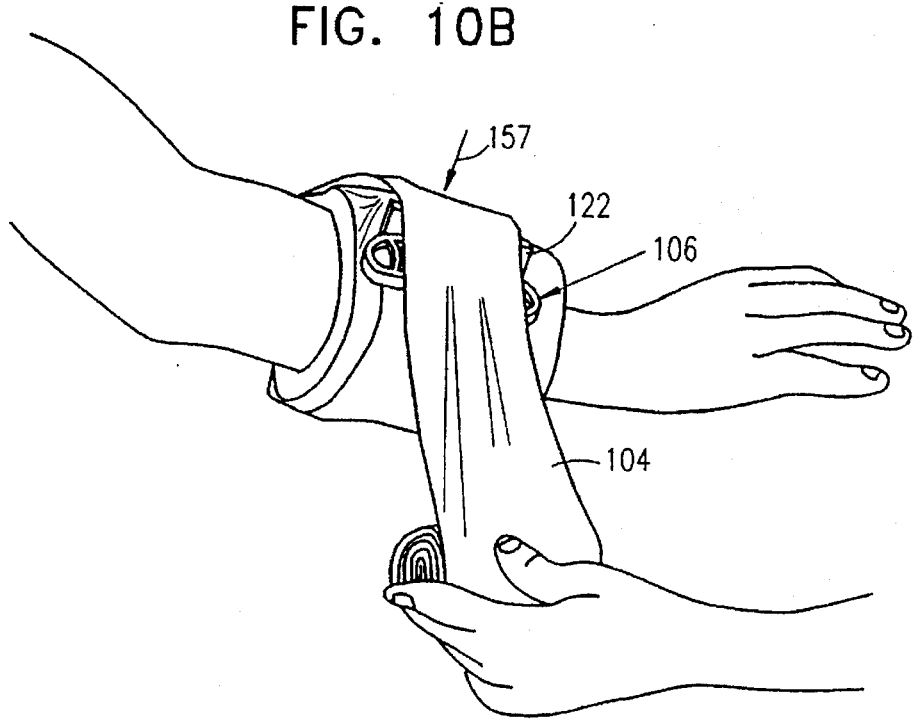

In FIG. 10B, web portion 104 has been wrapped around wounded limb 150 and is brought tightly against the long edge of base 122, and particularly notch 123, thereby applying a greater pressure against the wound generally in the direction of an arrow 157.

Stiffening ribs 128 substantially prevent the force caused by tightly pulling web portion 104 back against wings 124 from causing gap 130 to widen and inadvertently allowing web portion 104 to be pulled out of space 134.

Roughening ribs 132 (hidden by web portion 104 in FIG. 10A) increase the friction between web portion 104 and wings 124, thereby also helping prevent web portion 104 from inadvertently being pulled out of space 134.

Figure 11:
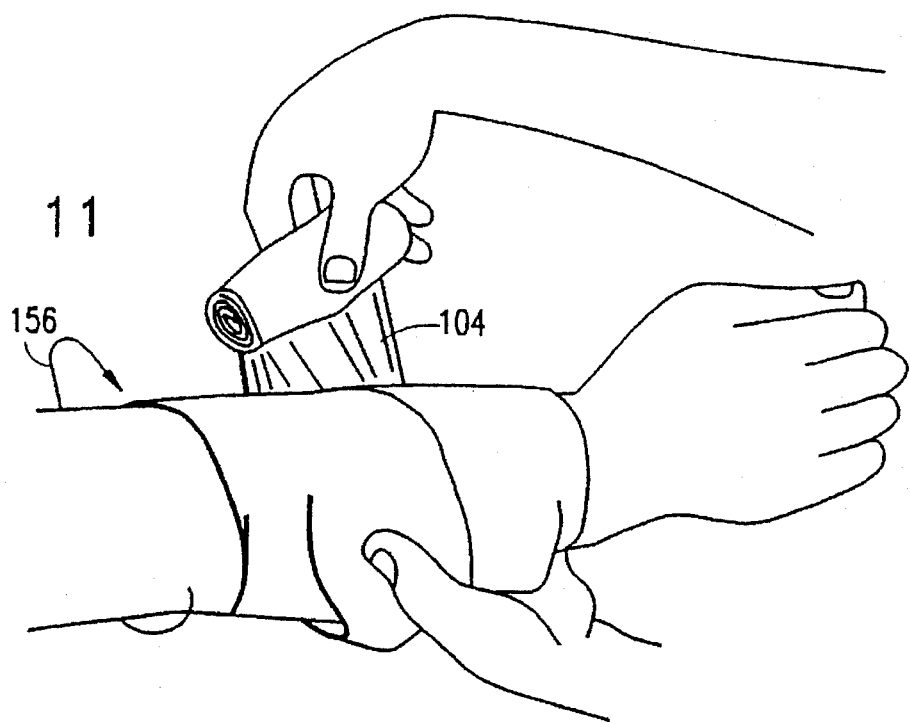

In FIG. 11, the user continues to wrap web portion 104 tightly around pressure enhancement member 106 and dressing 102 in the direction of arrow 156, thereby creating a secondary sterile dressing to the entire wound area without additional accessories.

Figure 12:
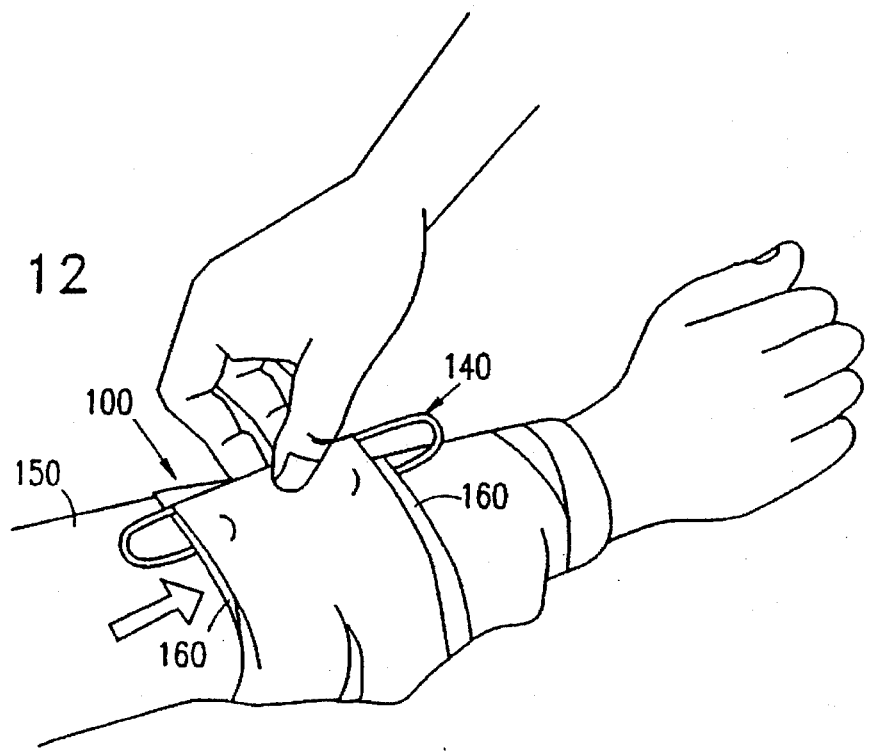

In FIG. 12, the user hooks hooking dowel 140 into some folds 160 formed in the wrapping of web portion 104, thereby securing bandage 100 around wounded limb 150.

Figure 13:
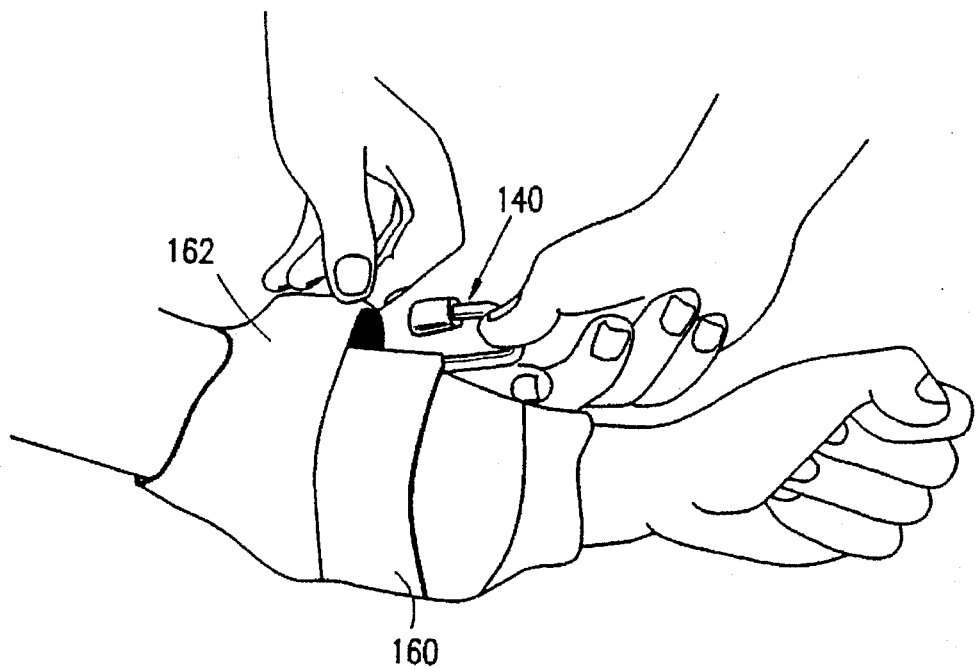
FIGS. 13 and 14 are simplified pictorial illustrations of applying a tourniquet to a wound using the bandage of FIG. 3.
Figure 14:
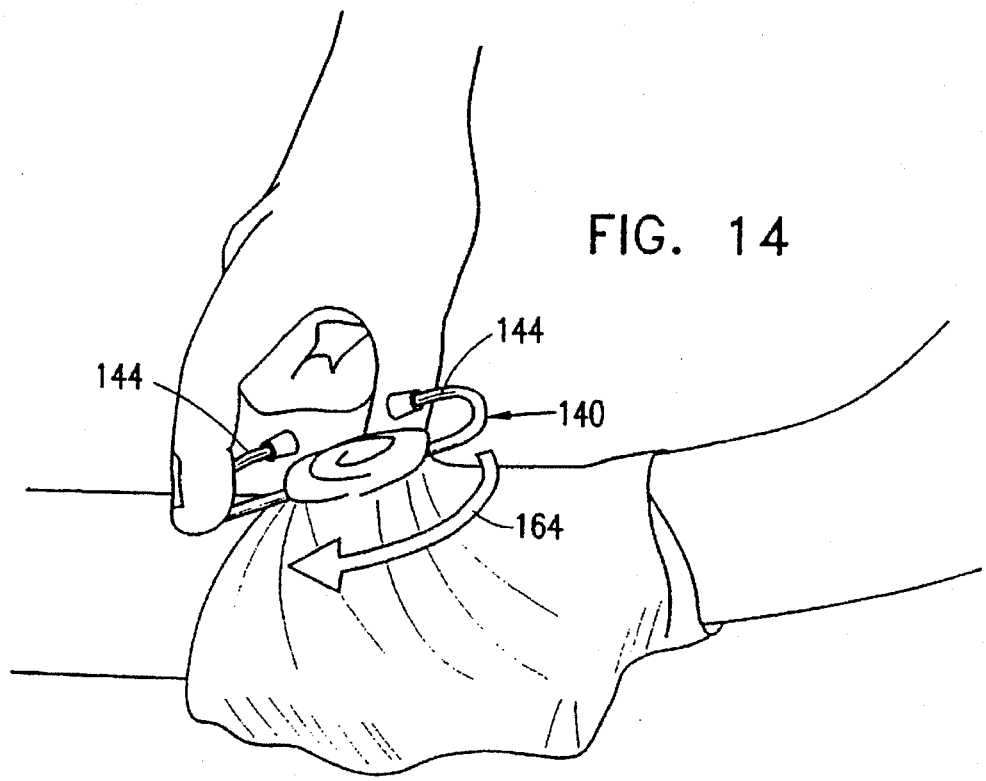

Bandage 100 may be used as a tourniquet, if such an application is necessary. Reference is now made to FIGS. 13 and 14 which illustrate applying a tourniquet to wounded limb 150 using bandage 100.

In FIG. 13, the user unhooks hooks 144 from folds 160, and hooks dowel 140 to some previous layers 162 of web portion 104, typically about 5 cm above the wound on an artery proximate to the wound. As shown in FIG. 14, the user then grasps hooks 144 of hooking dowel 140 and turns hooking dowel 140, such as in the direction of an arrow 164, thereby twisting web portion 104 and tightening it around wounded limb 150, and thereby applying a tourniquet to the wound.

Figure 15:
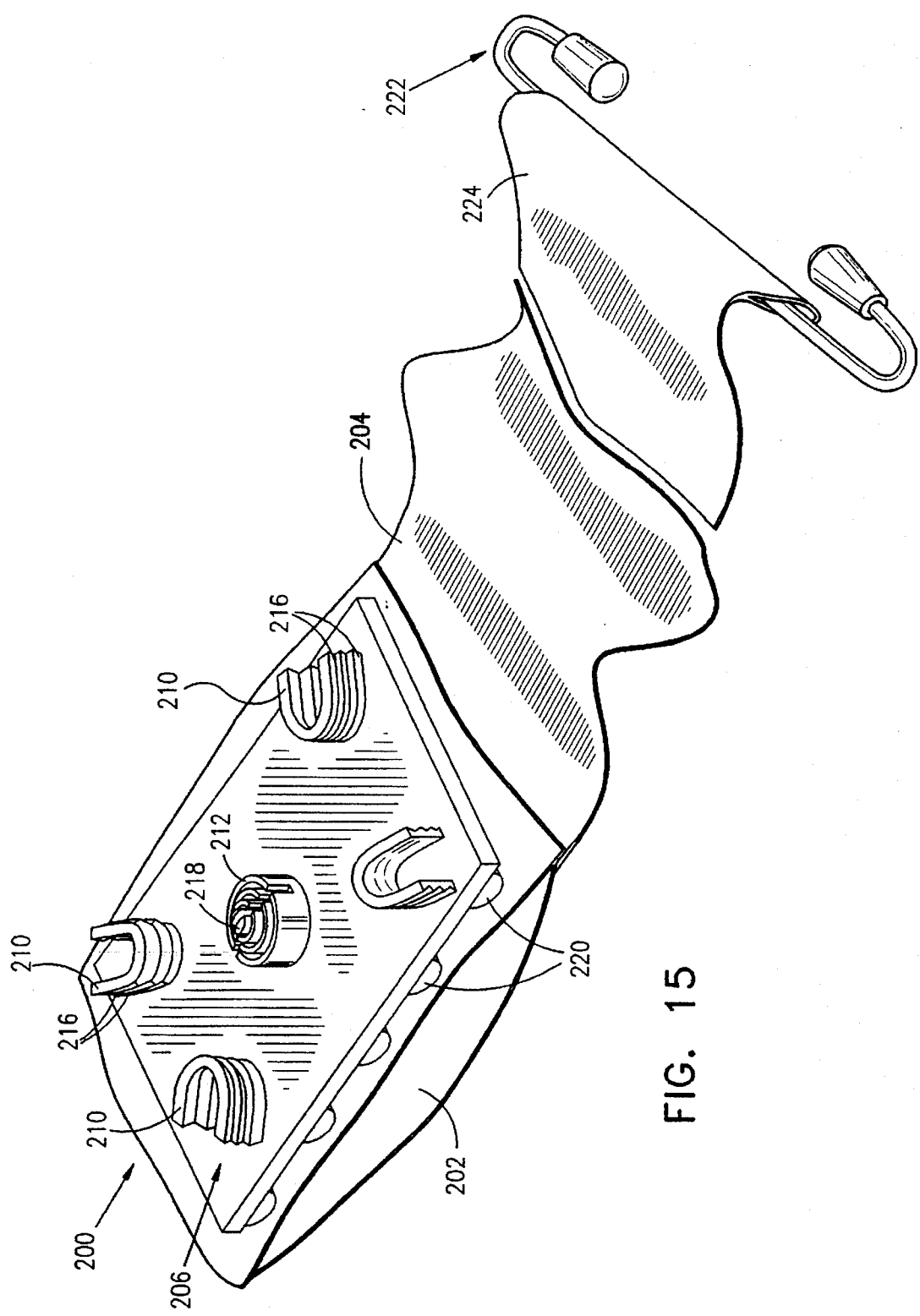
FIG. 15 is a partial simplified pictorial illustration of a bandage, constructed and operative in accordance with yet another preferred embodiment of the present invention.

Reference is now made to FIG. 15 which is a partial simplified pictorial illustration of a bandage 200, constructed and operative in accordance with yet another preferred embodiment of the present invention. Bandage 200 includes a sterile dressing 202, a web portion 204 and a pressure enhancement member 206.

Pressure enhancement member 206 comprises at least one, and preferably a plurality of wrapping elements, such as outer wrapping stubs 210 and at least one central wrapping stub 212, for wrapping web portion 204 therearound, as is described hereinbelow with reference to FIGS. 16-19. In the embodiment illustrated in FIG. 15, four outer wrapping stubs 210 and one central wrapping stub 212 are arranged similarly to a five-point pattern of a playing die, and are fixedly mounted on a platform 214 of pressure enhancement member 206.

Outer wrapping stubs 210 are shown in FIG. 15 with a U-shaped cross section, although they may have any other shape suitable for wrapping web portion 204 therearound. Stubs 210 and 212 may be roughened, such as being provided with furrows 216, for enhancing friction and wrapping tightness between web portion 204 and stubs 210 and 212.

Central wrapping stub 212 may be provided with a central notch 218 which is preferably oriented generally in the same direction as web portion 204, as shown in FIG. 15. Pressure enhancement member 206 also preferably includes a plurality of elongate bars 220 fixedly located on the underside of platform 214, for enhancing pressure applied on a wound.

Pressure enhancement member 206 is preferably constructed of medically accepted rigid materials, such as a structural plastic or silicone.

As seen in FIG. 15, a hooking dowel 222 is preferably attached to an end 224 of web portion 204. Hooking dowel 222 is substantially similar to hooking dowel 140 of bandage 100, described hereinabove with reference to FIG. 3.

Figure 16:
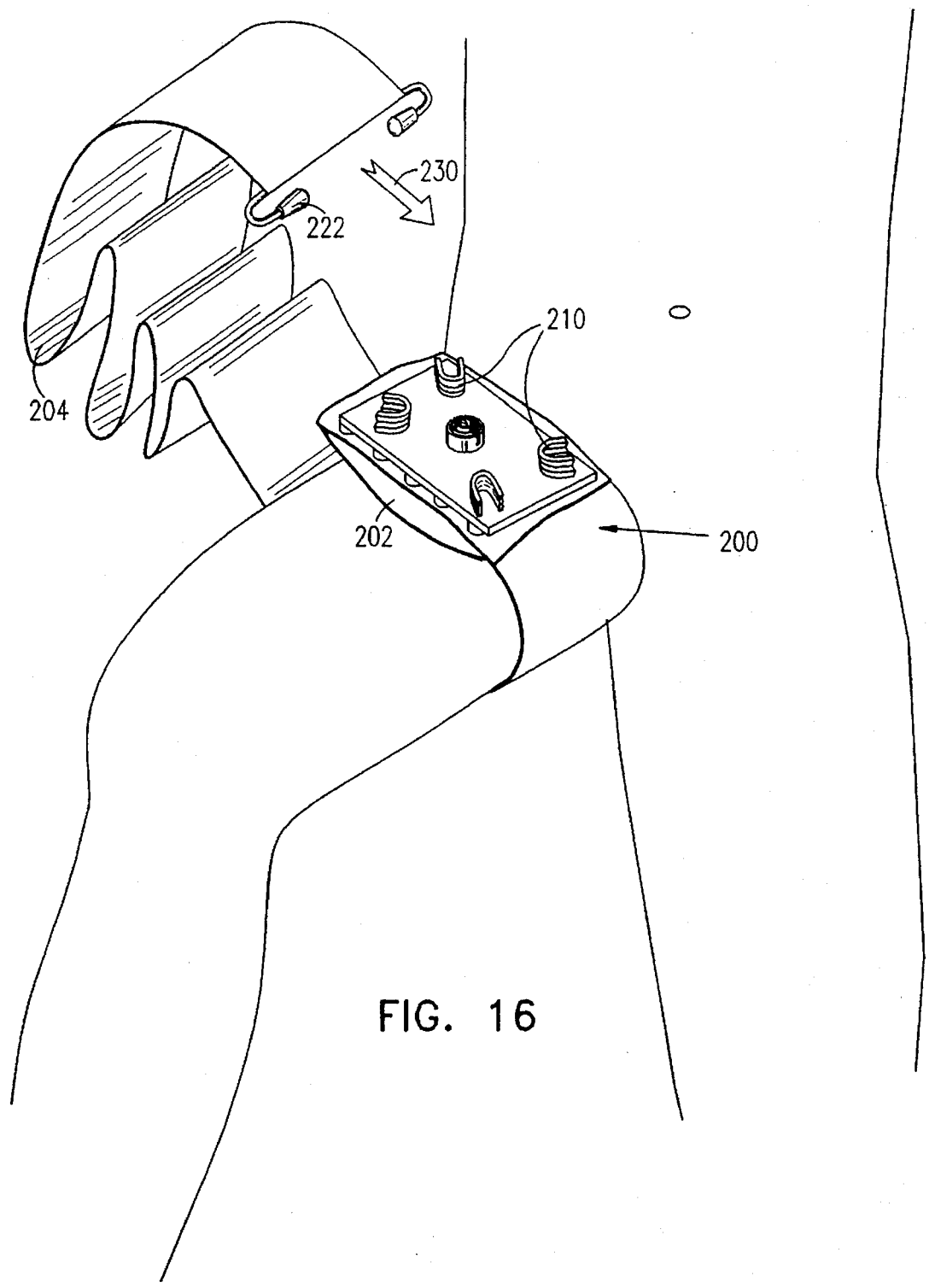
FIGS. 16–19 are simplified pictorial illustrations of bandaging a wound using the bandage of FIG. 15.

Reference is now made to FIGS. 16-19 which illustrate bandaging a wound, such as a wound to the femoral artery, using bandage 200. In FIG. 16, dressing 202 of bandage 200 is placed on the wound site on an upper portion of the thigh, and web portion 204 is wrapped partially around the thigh in the direction of an arrow 230.

Figure 17:
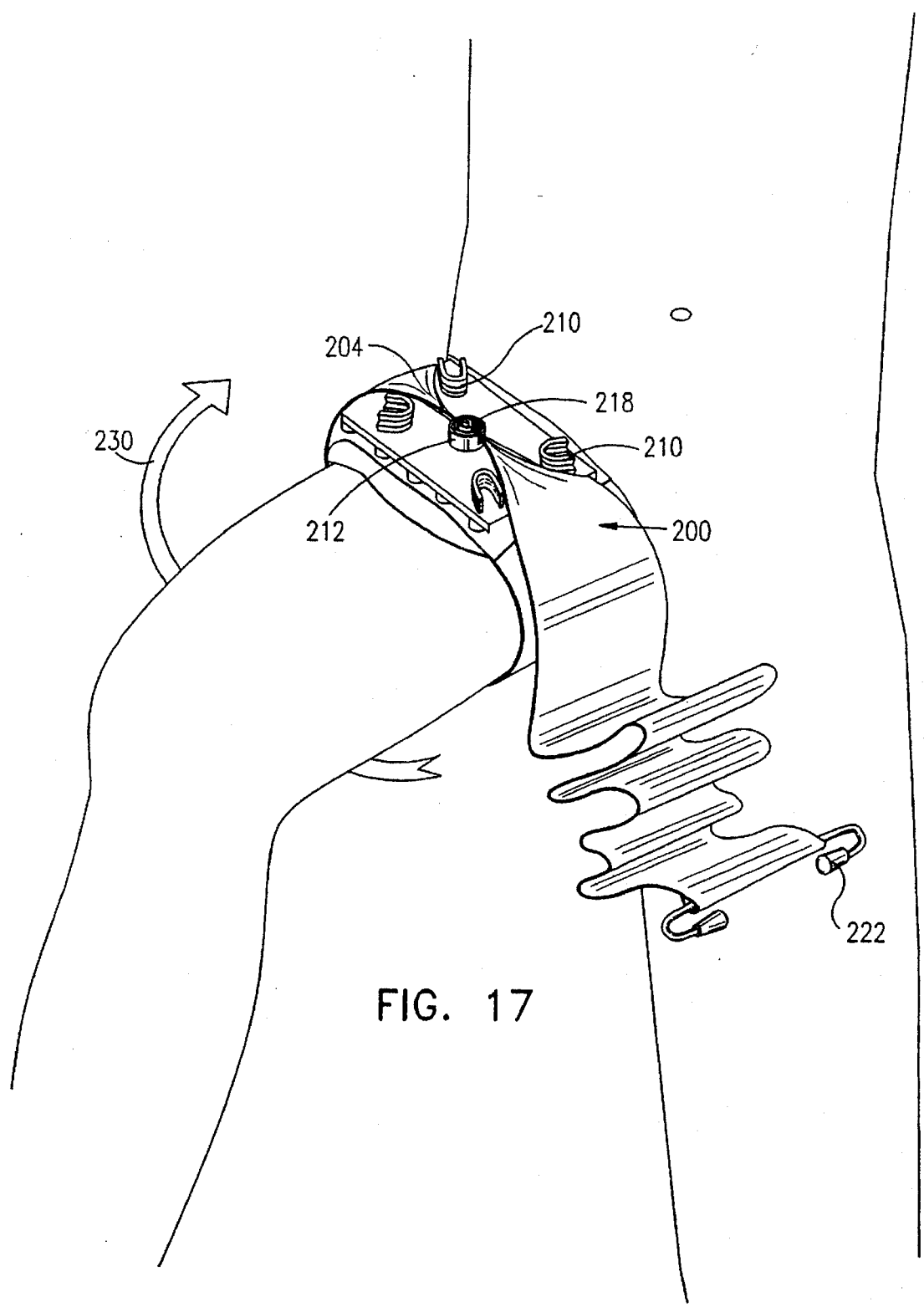

In FIG. 17, web portion 204 is tightly wrapped around the thigh and forced into notch 218 of central wrapping stub 212. Thus, web portion 204 is tightly pinched and held by central wrapping stub 212. Outer wrapping stubs 210 serve to guide web portion 204 in the wrapping process. As seen in FIG. 17, web portion 204 is further wrapped around the thigh in the direction of arrow 230.

Figure 18:
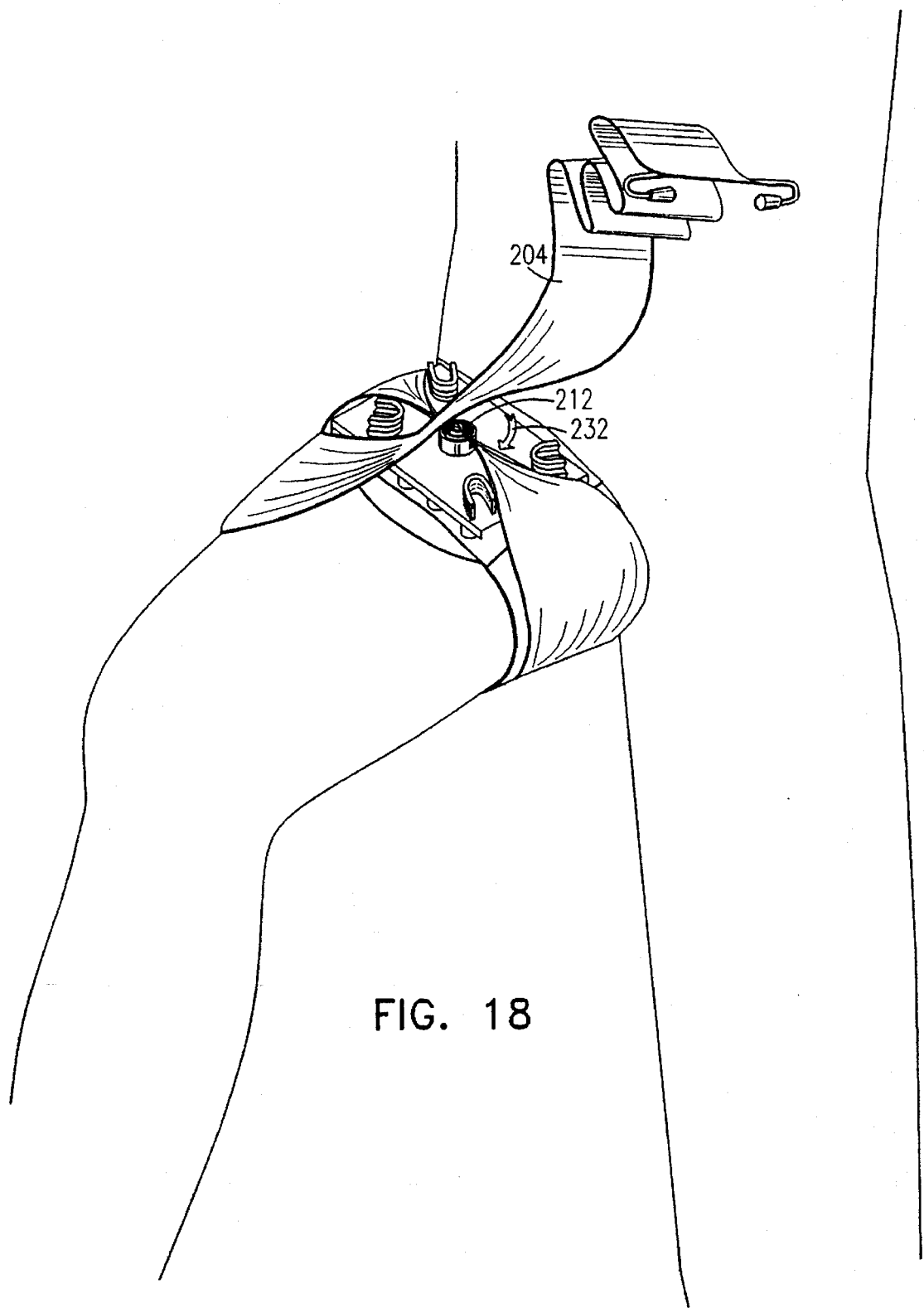
Figure 19:
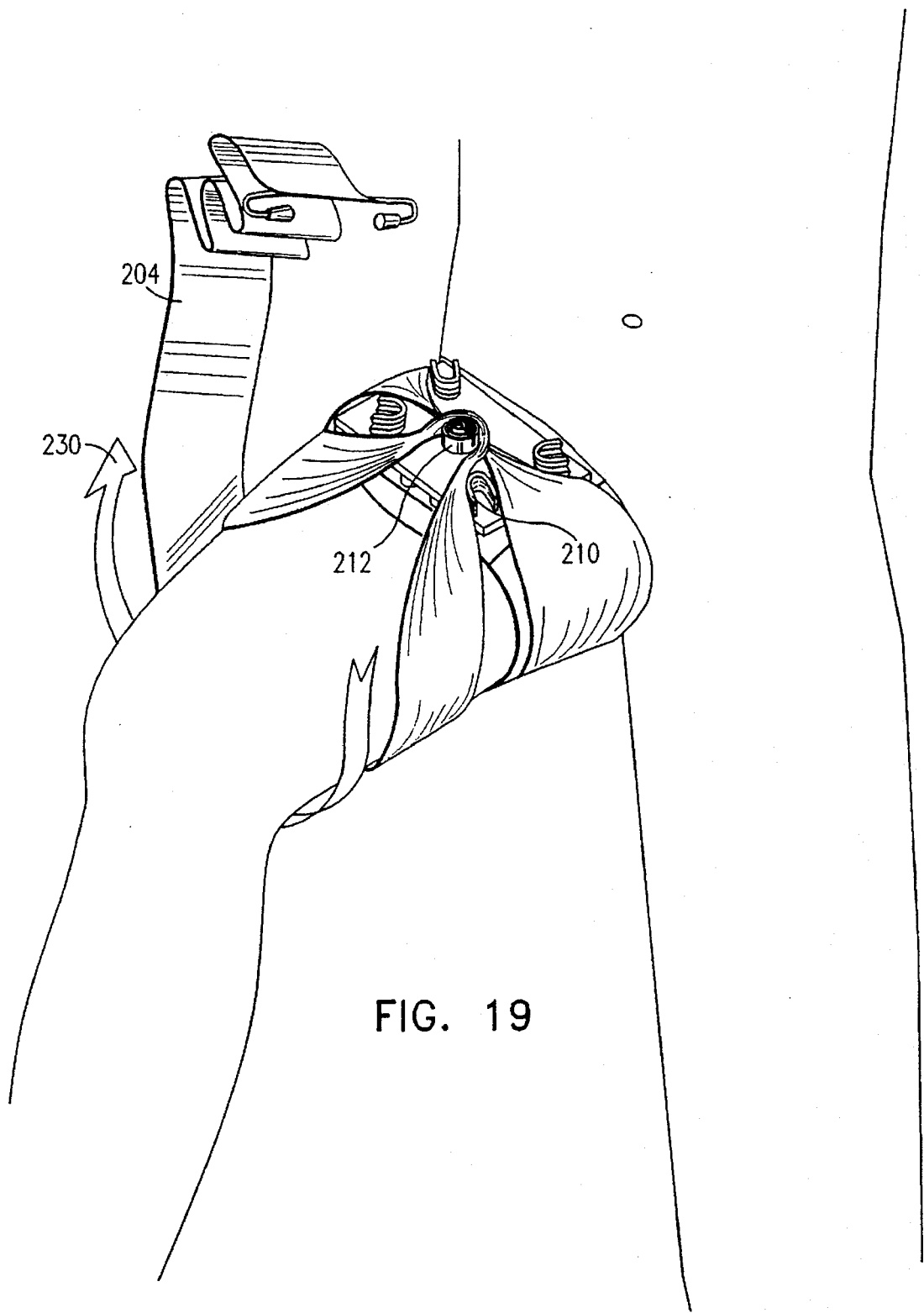

In FIG. 18, web portion 204 is further wrapped around the thigh and turned around the outer surface of central wrapping stub 212 in the direction of an arrow 232. In FIG. 19, web portion 204 is wrapped around and against one of the outer wrapping stubs 210, and then further wrapped around the thigh in the direction of arrow 230. It is appreciated that web portion 204 may be additionally or alternatively wrapped around the hips.

It is appreciated that wrapping stubs 210 and 212 may be used for wrapping and tightening web portion 204 in a variety of ways other than those illustrated in FIGS. 16-19. It is further appreciated that hooking dowel 222 may be used to apply a tourniquet similarly as described hereinabove for the embodiment of FIG. 3.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited to what has been particularly shown and described hereinabove. Rather, the scope of the present invention is defined only by the claims that follow:

I claim:

1. For use in a bandage comprising a sterile dressing and a web portion attached to and extending from said sterile dressing, a pressure enhancement member comprising:

a base; and at least one wrapping element generally perpendicular to said base, said at least one wrapping element having a gap, wherein said pressure enhancement member is attached to a non-wound-side surface of said sterile dressing, and said at least one wrapping element is arranged for wrapping therearound by said web portion;

wherein when said web portion is wrapped in a first direction around a limb having thereon a wound, and forced through said gap, and said web portion is then wrapped around said at least one wrapping element in a second direction, said pressure enhancement member applies a pressure on said dressing, thereby causing said dressing to apply a local pressure on said wound, and subsequent wrappings of said web portion on said pressure enhancement member, on previous wrappings of said web portion and on said limb, increase said local pressure on said wound.

2. A pressure enhancement member according to claim 1 and wherein at least one of said base and said at least one wrapping element has a notch formed thereon, wherein at least one of said subsequent wrappings of said web portion is wrapped against said notch.

3. A pressure enhancement member according to claim 1 and wherein said pressure enhancement member comprises at least two wings which are separated from each other by said gap.

4. A pressure enhancement member according to claim 3 and wherein said wings are resilient in a direction which facilitates forcing said web portion through said gap, and wherein said wings are configured such that once said web portion is forced through said gap, said web portion is substantially prevented from escaping said gap inadvertently.

5. A pressure enhancement member according to claim 1 and comprising at least one stiffening rib which stiffens said pressure enhancement member.

6. A pressure enhancement member according to claim 1 and wherein said at least one wrapping element is roughened.

7. A pressure enhancement member according to claim 1 and comprising a plurality of wrapping elements arranged in a pattern such that said web portion is wrappable around and between said wrapping elements.

8. A bandage comprising:
a sterile dressing;
a web portion attached to and extending from said sterile dressing; and
a pressure enhancement member attached to a non-wound-side surface of said sterile dressing, said pressure enhancement member comprising a base and at least one wrapping element generally perpendicular to said base, said at least one wrapping element having a gap, and said at least one wrapping element being arranged for wrapping therearound by said web portion;
wherein when said web portion is wrapped in a first direction around a limb having thereon a wound, and forced through said gap, and said web portion is then wrapped around said at least one wrapping element in a second direction, said pressure enhancement member applies a pressure on said dressing, thereby causing said dressing to apply a local pressure on said wound, and subsequent wrappings of said web portion on said pressure enhancement member, on previous wrappings of said web portion and on said limb, increase said local pressure on said wound.

9. A bandage according to claim 8 and wherein said base has a notch formed therein, wherein at least one of said subsequent wrappings of said web portion is wrapped against said notch.

10. A bandage according to claim 8 and wherein said pressure enhancement member comprises at least two wings which are separated from each other by said gap.

11. A bandage according to claim 10 and wherein said wings are resilient in a direction which facilitates forcing said web portion through said gap, and wherein said wings are configured such that once said web portion is forced through said gap, said web portion is substantially prevented from escaping said gap inadvertently.

12. A bandage according to claim 8 and wherein said at least one wrapping element is roughened.

13. A bandage according to claim 8 and comprising a plurality of wrapping elements arranged in a pattern such that said web portion is wrappable around and between said wrapping elements.

14. A bandage according to claim 8 and further comprising a hooking dowel attached to an end of said web portion, for securing said bandage after wrapping around said limb.

15. A bandage according to claim 14 and wherein said hooking dowel comprises at least one prong which engages a portion of said web portion.

16. A bandage according to claim 14 and wherein said hooking dowel is twisted together with a portion of said web portion, thereby applying a tourniquet to said wound.

17. A method for dressing a wound on a limb, said method comprising the steps of:
providing a bandage, said bandage comprising:
a sterile dressing;
a web portion attached to and extending from said sterile dressing; and
a pressure enhancement member attached to a non-wound-side surface of said sterile dressing, said pressure enhancement member comprising a base and at least one wrapping element generally perpendicular to said base, said at least one wrapping element having a gap, and said at least one wrapping element being arranged for wrapping therearound by said web portion;
wrapping said web portion in a first direction around said limb;
forcing said web portion through said gap;
wrapping said web portion around said at least one wrapping element in a second direction, thereby causing said pressure enhancement member to apply a pressure on said dressing, thereby causing said dressing to apply a local pressure on said wound; and
wrapping said web portion around said limb and said pressure enhancement member, thereby causing subsequent wrappings of said web portion on said pressure enhancement member, on previous wrappings of said web portion and on said limb, to increase said local pressure on said wound.

18. A method according to claim 17 and wherein said second direction is generally opposite to said first direction.

19. A method according to claim 17 and wherein said second direction is generally perpendicular to said first direction.

20. A method according to claim 17 and wherein said base is generally parallel to said wound when wrapping said web portion in said first direction, and wherein said base is brought generally perpendicular to said wound when wrapping said web portion in said second direction.

* * * * *